US00PP12930P2

(12) United States Plant Patent
Segers

(10) Patent No.: US PP12,930 P2
(45) Date of Patent: Sep. 10, 2002

(54) ROSE PLANT NAMED 'PRERACLIM'

(75) Inventor: Theodorus A. Segers, Hoofddorp (NL)

(73) Assignee: Prego Royalty, B.V., Naaldwijk (NL)

( * ) Notice: Subject to any disclaimer, the term of this patent is extended or adjusted under 35 U.S.C. 154(b) by 84 days.

(21) Appl. No.: 09/664,135

(22) Filed: Sep. 19, 2000

(51) Int. Cl.[7] ..... A01H 5/00
(52) U.S. Cl. ..... Plt./140
(58) Field of Search ..... Plt./140

(56) References Cited

PUBLICATIONS

UPOV–ROM GTITM Computer Database, 2001/04, GTI Jouve Retrieval Software, citation for 'Preaclim'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A distinctive cultivar of Hybrid Tea rose plant named 'Preraclim', characterized by its dark green leaves; long and strong stems; large dark red-colored flowers; and excellent postproduction longevity.

1 Drawing Sheet

BACKGROUND OF THE INVENTION

The present invention relates to a new and distinct cultivar of Hybrid Tea Rose plant, botanically known as *Rosa hybrida*, and hereinafter referred to by the cultivar name Preraclim.

The new cultivar is a product of a planned breeding program conducted by the Inventor in Rijsenhout, The Netherlands. The objective of the breeding program was to develop new cut Rose cultivars with attractive flower colors, long and strong stems, dark green leaves, good production during the winter, and good postproduction longevity.

The new cultivar originated from a cross made by the Inventor in 1996 of two proprietary selections. The proprietary selection 94-316 was the female, or seed, parent and the proprietary selection 95-274 was the male, or pollen, parent. The cultivar Preraclim was discovered and selected by the Inventor as a flowering plant within the progeny of the stated cross in a controlled environment in Rijsenhout, The Netherlands.

Asexual reproduction of the new cultivar by cuttings taken at Rijsenhout, The Netherlands, has shown that the unique features of the new cultivar are stable and reproduced true to type in successive generations of asexual reproduction.

SUMMARY OF THE INVENTION

The following traits have been repeatedly observed and are determined to be the unique characteristics of 'Preraclim'. These characteristics in combination distinguish the new Hybrid Tea rose as a new and distinct cultivar:

1. Dark green leaves.
2. Long and strong stems.
3. Large dark red-colored flowers.
4. Excellent postproduction longevity.

Plants of the Hybrid Tea Rose can be compared to plants of the cultivar Pekcoujenny, not patented. In side-by-side comparisons conducted by the Inventor in De Kwakel, The Netherlands, plants of the cultivar differed from plants of the cultivar Pekcoujenny in the following characteristics:

1. Plants of the new Hybrid Tea Rose are more freely branching than plants of the cultivar Pekcoujenny.

2. Plants of the new Hybrid Tea Rose have many more petals per flower than plants of the cultivar Pekcoujenny.

3 . Plants of the new Hybrid Tea Rose have more flowers per stem than plants of the cultivar Pekcoujenny.

4. Plants of the new Hybrid Tea Rose are more productive during the winter than plants of the cultivar Pekcoujenny.

5. Cut flowers of plants of the new Hybrid Tea Rose have much better postproduction longevity than cut flowers of plants of the cultivar Pekcoujenny.

Plants of the new Hybrid Tea Rose have not been observed under all possible environmental conditions. The phenotype may vary significantly with variations in environment such as temperature, light, water status and/or fertilizer type and rate, without, however, any variance in genotype.

BRIEF DESCRIPTION OF PHOTOGRAPH

The accompanying colored photograph illustrates the new Hybrid Tea Rose plant, showing the colors as true as it is reasonably possible to obtain in colored reproductions of this type. Colors in the photograph may differ slightly from the color values cited in the detailed botanical description which more accurately describe the actual colors of the new miniature rose. The photograph comprises a top perspective view of typical flowers and leaves of the new Hybrid Tea Rose grown in Rijsenhout, The Netherlands.

DETAILED BOTANICAL DESCRIPTION

The following observations and measurements describe plants grown in Rijsenhout, The Netherlands, in glass-covered greenhouses with average day temperatures of 18° C. and average night temperatures of 17° C. Flowering stems used in the photographs and the description were about seven weeks old. In the following description, color references are made to The Royal Horticultural Society Colour Chart, 1995 edition, except where general terms of ordinary dictionary significance are used.

Classification:

*Botanical.*—*Rosa hybrida* cultivar Preraclim.
*Commercial.*—Hybrid Tea Rose used as a cut flower.

*Parentage:*

*Female, or seed, parent.*—*Rosa hybrida* proprietary selection 94-316.

*Male, or pollen, parent.*—*Rosa hybrida* proprietary selection 95-274.

Propagation:

*Type.*—Cuttings.

*Time to initiate roots.*—About 12 days at 25° C.

*Time to develop roots.*—About 25 days at 25° C.

*Root description.*—Fine, fibrous and well-branched.

Plant description:

*Form.*—Upright; narrow; bushy.

*Plant height.*—About 90 cm.

*Plant width.*—About 40 cm.

*Growth habit.*—Moderately vigorous.

*Stem and lateral branches.*—Quantity of lateral branches: Freely branching; typically 4 to 5 per plant. Lateral branch length: About 70 cm. Lateral branch diameter: About 3.5 cm. Internode length: About 6 cm. Texture: Smooth. Color: 137B. Prickles: Amount: Moderate. Height: About 7 mm. Color: Apex, 164A, fading towards 164B at base.

*Foliage description.*—Leaves arranged alternately, compound with typically five to seven leaflets per leaf, generally symmetrical, abundant, and flat in aspect; about 12 compound leaves per lateral branch. Leaf length, seven-leaflet leaves: About 18 cm. Leaf width, seven-leaflet leaves: About 13.5 cm. Leaflet shape: Ovate. Leaflet apex: Acute. Leaflet base: Obtuse. Leaflet margin: Serrate. Leaflet texture: Smooth, shiny. Petiole length: To base of lower leaflet: About 4 cm. To base of terminal leaflet: About 10 cm. Petiole diameter: About 3 mm. Petiole texture: Smooth. Color: Young foliage, upper surface: 137A. Young foliage, lower surface: 191A. Mature foliage, upper surface: 137A; venation, 139A. Mature foliage, lower surface: 137C; venation, 146B. Petiole: 137A.

Flower description:

*Flower type and habit.*—Large dark red flowers. Consistently symmetrical rosette flowers. Freely and recurrent flowering. Flowers arranged singly at terminal apices or in sprays of 2 to 3 flowers per spray; 4 to 12 flowers per plant at a time. Flowers persistent.

*Flowering season/time to flower.*—Year-round under greenhouse conditions. Depending on environmental conditions and season, time to flower is about seven weeks.

*Flower diameter.*—About 8 cm.

*Flower depth* (*height*).—About 5.5 cm.

*Flower longevity on plant.*—About 16 days.

*Flower longevity as a cut flower.*—About 15 days.

*Fragrance.*—Faint, typical of Rosa.

*Flower buds* (*when opening*).—Shape: Oblong. Length: About 4.5 cm. Diameter: About 3.5 cm. Color: 60A.

*Petals.*—Quantity: About 60 petals per flower arranged in at least five to six whorls. Length, outer petals: About 5 cm. Width, outer petals: About 5.5 cm. Shape: Orbicular. Apex: Mucronate. Margin: Entire, undulate, slightly reflexed. Texture: Smooth, satiny. Color: When opening, upper surface: 46A. When opening, lower surface: 53D. Fully opened, upper surface: 46A; color does not fade with subsequent development. Outer petals, may have greenish tinge towards the base. Fully opened, lower surface: 53D.

*Sepals.*—Quantity: Five. Calyx length: About 4 cm. Calyx diameter: About 3.8 cm. Shape: Elongate, subulate. Apex: Aristate. Texture: Smooth. Color: Upper surface: 144A. Lower surface: 191A.

*Peduncles.*—Strength: Strong. Aspect: Erect. Length: About 9.5 cm. Color: 147B.

*Reproductive organs.*—Stamens: Quantity: About 103 per flower. Anther length: About 2.6 mm. Anther shape: Ovate. Anther color: 12A. Pollen amount: Moderate. Pollen color: 10A. Pistils: Quantity: About 108 per flower. Style length: About 9 mm. Style color: 8C. Stigma color: 8A. Ovary color: 19C.

*Fruit/hips.*—Shape: Pitcher. Color: Green.

*Seed.*—Length: About 7 mm. Diameter: About 4 mm. Color: 159B.

Disease resistance: Moderate resistance to Powdery Mildew has been observed on plants grown under commercial greenhouse production conditions.

It is claimed:

1. A new and distinct Hybrid Tea Rose plant named 'Preraclim', as illustrated and described.

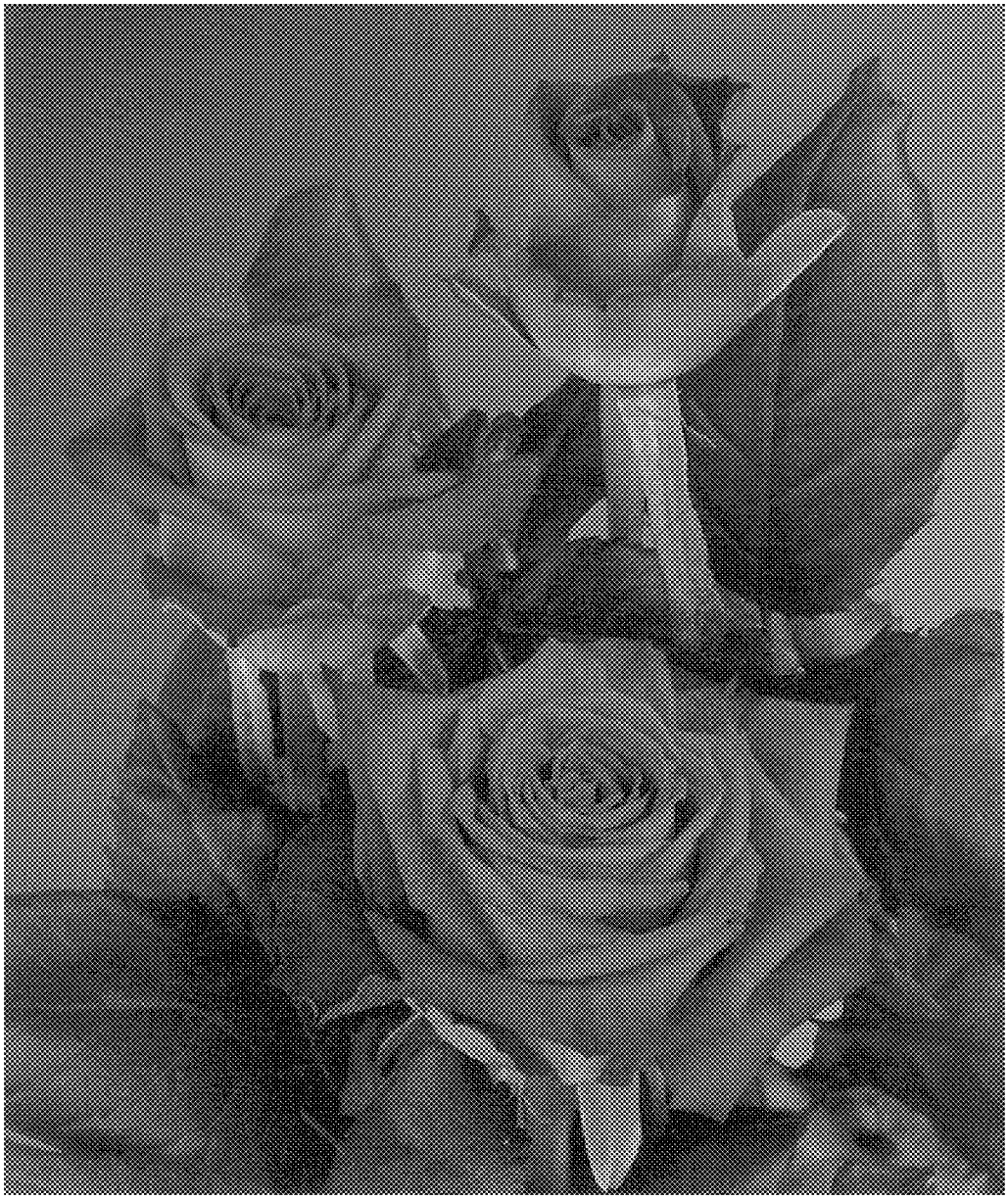

* * * * *